United States Patent [19]

Takahashi et al.

[11] Patent Number: 4,574,264

[45] Date of Patent: Mar. 4, 1986

[54] THIN FILM OXYGEN SENSOR WITH MICROHEATER

[75] Inventors: Hideaki Takahashi; Haruyoshi Kondo; Takashi Takeuchi; Kiyoharu Hayakawa; Hideaki Muraki, all of Aichi, Japan

[73] Assignee: Kabushiki Kaisha Toyota Chuo Kenkyusho, Aichi, Japan

[21] Appl. No.: 552,201

[22] Filed: Nov. 15, 1983

[30] Foreign Application Priority Data

Nov. 17, 1982 [JP] Japan .................................. 57-200390

[51] Int. Cl.$^4$ ............................................. H01L 7/00
[52] U.S. Cl. .......................................... 338/34; 73/23; 73/27 R; 422/98
[58] Field of Search .................... 338/34; 73/23, 27 R; 422/98

[56] References Cited

U.S. PATENT DOCUMENTS

| | | | |
|---|---|---|---|
| 3,479,257 | 11/1969 | Shaver | 204/274 X |
| 4,187,486 | 2/1980 | Takahashi et al. | 338/34 |
| 4,224,280 | 9/1980 | Takahama et al. | 338/34 X |
| 4,242,303 | 12/1980 | Takahashi et al. | 338/34 X |
| 4,259,292 | 3/1981 | Ichinose et al. | 338/34 X |
| 4,313,338 | 2/1982 | Abe et al. | 338/34 X |
| 4,343,768 | 8/1982 | Kimura | 422/98 X |
| 4,351,182 | 9/1982 | Schmidberger | 338/34 X |
| 4,396,899 | 8/1983 | Ohuo | 338/34 |

FOREIGN PATENT DOCUMENTS

| | | | |
|---|---|---|---|
| 56-51656 | 5/1981 | Japan | 338/34 |
| 56-112638 | 9/1981 | Japan | 338/34 |

OTHER PUBLICATIONS

Heiland, "Homogeneous Semiconducting Gas Sensors", Sensors and Actuators, vol. 2, #4, Sep. 1982, pp. 343-359.

Primary Examiner—C. L. Albritton
Assistant Examiner—M. M. Lateef

[57] ABSTRACT

A thin film oxygen sensor with a microheater incorporates an oxide semiconductor and has an integral structure of a sensor portion and a heater portion, wherein a porous catalyst layer is formed on a surface of the sensor portion, and a thickness and an average pore diameter of the catalyst layer are determined such that a ratio of the thickness to the average pore diameter falls within a range of 50 to 3,000. The oxygen sensor has good reproducibility, high stability, and high sensitivity for changing a resistance in response to a change in an oxygen content in an atmosphere. The oxygen sensor can be manufactured at low cost and has a compact construction.

5 Claims, 13 Drawing Figures

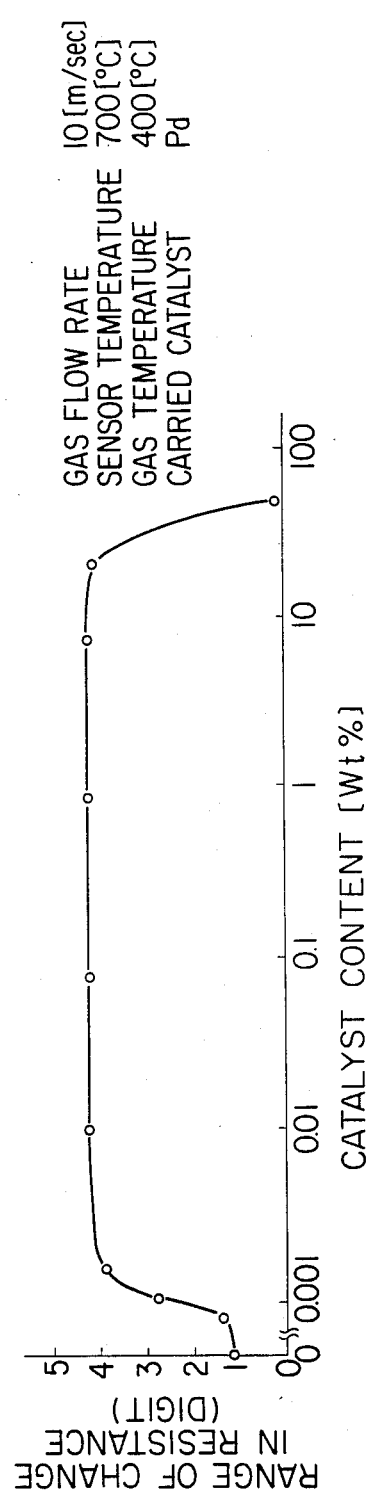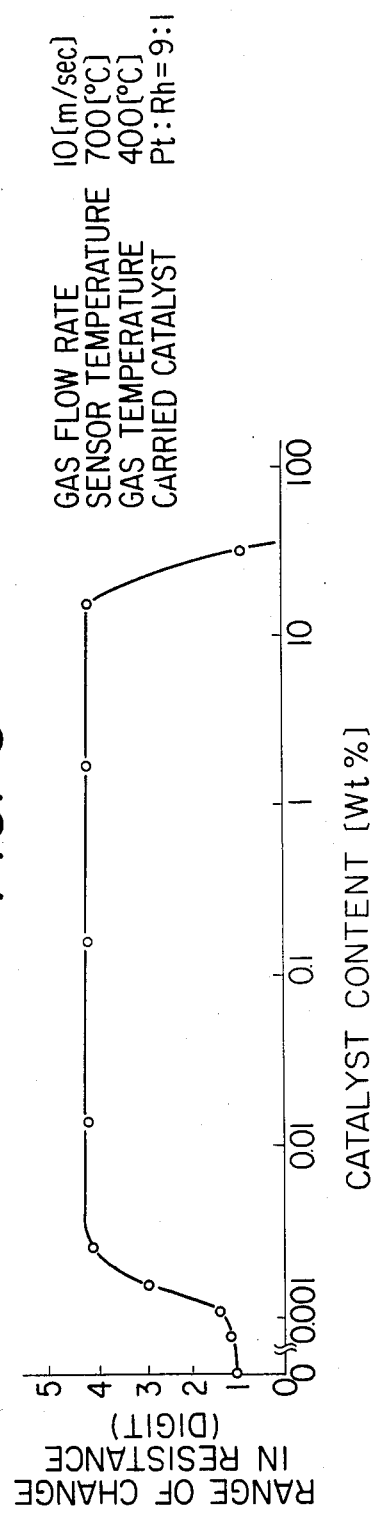

THIN FILM OXYGEN SENSOR WITH MICROHEATER

BACKGROUND OF THE INVENTION

The present invention relates to a thin film oxygen sensor incorporating an oxide semiconductor and having a structure wherein a sensor element is integrally formed with a heater element.

An exhaust gas cleaning system has been known as a method for improving fuel consumption of an internal combustion engine of an automobile and for decreasing toxic components in an exhaust gas, wherein the concentration of oxygen contained in the exhaust gas is detected, and the air or fuel quantity is controlled in accordance with the detection signal. In particular, the present invention relates to an improvement in an oxygen sensor (especially, of a thin film oxygen sensor of an oxide semiconductor) used for such an exhaust gas cleaning system.

Conventional problems are described hereinafter. Oxide elements such as $TiO_2$, $CoO$, $CeO_2$, $Nb_2O_5$ and $SnO_2$ are used for oxide semiconductor type ceramic oxygen sensors (of resistance change type) which carry a catalyst such as Pt. When the characteristics of these oxygen sensors are actually examined by being placed in an exhaust gas from an internal combustion engine, and changes in resistances of the senors are measured when the air-fuel ratio changes, the characteristics of such changes in resistance are greatly different in the following cases: (1) when the engine is started; (2) when the exhaust gas is warmed; and (3) when the exhaust gas is sufficiently heated to a high temperature. The operation state of the internal combustion engine varies; the engine is operated at random in a deceleration, acceleration or constant speed mode. For this reason, the temperature and flow rate of the exhaust gas greatly vary, so that the components of the exhaust gas reaching the oxygen sensor greatly vary.

(a) Application of Oxygen Sensor

A resistance-change type oxygen sensor (resistance $R_2$) using an oxide semiconductor is connected in series with a reference resistor (resistance $R_1$). A voltage $V_1$ is applied from a constant voltage source to the series circuit of the oxygen sensor and the reference resistor. An output voltage $V_2$ appearing across two ends of the sensor having the resistance $R_2$ is given as $V_2=\{R_2/(R_1+R_2)\}V_1$ in accordance with a change in the sensor resistance $R_2$. The output voltage $V_2$ is entered as data in an air-fuel ratio control computer and is compared with a reference voltage. The computer determines that the air-fuel ratio represents a "lean" (insufficience fuel) state when the output voltage is higher than the reference voltage. Otherwise, the computer determines that the air-fuel ratio represents a "rich" (excessive fuel) state. The fuel injection quantity is controlled in accordance with the determination result so as to always combust the fuel at the theoretical air-fuel ratio, thereby improving combustion efficiency.

The following methods are considered to improve precision in controlling the air-fuel ratio of the resistance-change type oxygen sensor:

(1) A thermistor is inserted in series with the sensor to compensate for temperature dependence.

(2) The sensor is heated to and kept at a predetermined temperature to decrease temperature dependency of control precision.

(3) Since the resistance of the oxide semiconductor greatly changes in accordance with an oxygen partial pressure, a catalyst is carried on the surface of and inside the sensor so as to completely combust a noncombusted gas, thereby greatly changing the oxygen partial pressure in the vicinity of the sensor.

(b) Response Control

In order to accurately detect a change in the air-fuel ratio of the engine, a thin film method unlike the conventional sintering method was used by the present inventors to manufacture a sensor in such a way as to improve the response characteristics of the sensor. As a result, the thin film sensor had a high speed response about 5 to 10 times that of the conventional sintered sensor.

When the sensor was mounted in an automobile driven in a test run, it was found that no problems occurred provided the engine speed was not less than 4,000 [rpm], but that controllability of the engine was degraded when the engine was operated at a low speed. This is caused by the fact that any slight difference between the cylinder injectors which control the fuel injection quantity results in variation in the air-fuel ratios of fuel quantities injected into the respective cylinders at a low speed of not more than 1,000 [rpm]. For example, when the quantity of fuel injected into the first cylinder differs from that injected into the second cylinder, the air-fuel ratio with respect to the first cylinder differs from that of the second cylinder since the quantity of air supplied to the first cylinder is the same as that supplied to the second cylinder. As a result, this difference is detected as a change in the air-fuel ratio by the sensor disposed in the common portion of the intake manifold, and the sensor having high speed response detects it as the variation of the air fuel ratio thus resulting in degradation of controllability.

In general, the sensor must have good sensitivity characteristics for accurately detecting a change in air-fuel ratio. However, when the response characteristics of the sensor are improved, it has an increased tendencey to be influenced by a distrubing signal, resulting in erroneous operation. Therefore, the response characteristics of the sensor must have a proper response range. An engine control sensor preferably has a response range from about 50 msec to 1000 msec.

(c) Cause of Poor Reproducibility and Low Stability

The present inventors examined why a resistance-change type oxygen sensor incorporating an oxide semiconductor had low stability and poor reproducibility.

A sintered $TiO_2$ sensor was mounted in an automobile which was subjected to a test run. This sensor was heated to and kept at by a built-in sensor a temperature of 700° C. to 800° C. and had a sufficient catalyst to increase activity.

The following phenomenon occasionally occurs when an engine is started and operated at a steady state and changes in resistance of the sensor are examined. Even if the resistance of the sensor is very small and the air-fuel ratio is given as lean, the sensor detects a similar result as if the air-fuel ratio of the engine was changed to a rich ratio.

It was found that noncombusted components such as soot or tar become attached to the surface of the sensor when the air-fuel ratio was set to a richer ratio (excess air factor $\lambda=0.5$ or less), thereby impairing stability and reproducibility. Further, even if the catalyst of the sensor is highly active, the gasoline cannot be completely vaporized, and can only be partially combusted at the start of engine operation. As a result, an unacceptably rich state can be obtained. Furthermore, since the temperature of the exhaust gas is low, incomplete combustion occurs. Therefore, even if the sensor is kept at a predetermined temperature, the noncombusted components become attached to the surface of the sensor when the sensor is exposed in a rich atmosphere. Although the noncombusted components attached on the surface of the sensor can be partially combusted when the sensor is heated, the noncombusted components may not be completely combusted. When some of the noncombusted components are left on the sensor, such residual components have a higher conductivity than $TiO_2$, which constitutes the sintered sensor. As a result, even if the resistance between sensor terminals is low, a similar signal is generated as if the rich atmosphere obtains.

In the conventional resistance-change type oxygen sensor having the structure wherein noncombusted components become attached to the surface of the sensor, it is found that poor reproducibility and low stability disables practical application.

SUMMARY THE INVENTION

The present invention has been made to solve the conventional problems described above, and has for its object to provide a compact, low-cost oxide semiconductor type thin film oxygen sensor with a microheater which has good reproducibility and high stability, wherein a resistance immediately changes in response to the amount of oxygen in the surrounding atmosphere.

In order to achieve the above object of the present invention, there is provided an oxygen sensor incorporating an oxide semiconductor and having an integral structure consisting of a sensor portion and a heater portion, wherein a porous catalyst layer is formed on a surface of said sensor portion to prevent noncombusted components from becoming attached to said surface of said sensor portion, the thickness of said catalyst layer and the average diameter of pores thereof being determined such that the ratio of said thickness of said catalyst layer to said average diameter of the pores thereof falls within a range from 50 to 3,000.

A catalyst component carried on the catalyst layer may be a material selected from the group consisting of palladium (Pd), rhodium (Rh), platinum (Pt) and a mixture of at least two thereof, and carried in an amount falling within a range from 0.001 to 50 [wt %].

An oxide semiconductor of the oxygen sensor comprises a thin layer formed of a material selected from the group consisting of $TiO_2$, $Nb_2O_5$, $CeO_2$ and $SnO_2$.

BRIEF DESCRIPTION OF THE DRAWINGS

FIGS. 1 to 3 show part of an oxygen sensor having an integral structure consisting of a heater portion and a sensor portion according to the present invention, in which FIG. 1 is a plan view thereof so as to show the sensor portion, FIG. 2 is a side view thereof, and FIG. 3 is a bottom view thereof so as to show the heater portion;

FIGS. 7 and 8, respectively, are graphs for explaining the degree of variation in the sensor resistance as a function of catalyst types and amounts in the respective catalyst layers coated on the sensor portions;

DETAILED DESCRIPTION OF THE INVENTION

Figure 1:
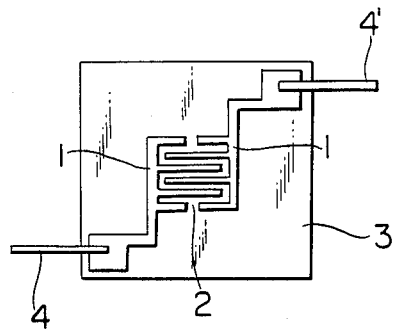

An oxygen sensor embodying the present invention preferably comprises: a layer carrying a catalyst on a porous coating base; electrodes; an oxide semiconductor type thin film whose resistance changes in accordance with the air-fuel ratio; an alumina substrate; a thin film heater for heating the sensor portion to a temperature up to about 800° C.; and a dense protective layer.

A method for manufacturing the oxygen sensor described above will be briefly described below. A thin $TiO_2$ film (thickness of 1,000 Å to 5 μm is formed by a high-rate RF sputtering apparatus on one major surface of an alumina substrate (thickness of 0.1 to 0.3 mm and area of 30 mm ×30 mm). A Pt electrode film is deposited on the thin $TiO_2$ film to a thickness of about 1 μm. A heater material such as Pt which has good heat resistance characteristics is sputtered on the other major surface of the alumina substrate. The interdigital Pt electrodes and the heater electrodes are connected to Pt lead wires, respectively. Thereafter, a porous ceramic film carrying the catalyst is formed on a prospective sensor portion of the thin oxide film to a thickness of about 20 to 5,000 μm. The porosity of the porous ceramic film is given to be 20 to 80%. On the other hand, a dense alumina adhesive is applied to cover the heater surface to a thickness of 50 to 1,000 μm so as to protect the heater.

The thin film oxygen sensor with the microcomputer according to the present invention is normally kept at a predetermined temperature by the heater. Even if changes in the temperature and flow rate of the exhaust gas occur, the change in sensor temperature deviates by as little as within the range of 0.1 %. Noncombusted molecules and combustible materials in the noncombusted state which reach the sensor are constrained to pass through the porous ceramic layer which carries the catalyst, so that the noncombusted components are subject to gas reaction and hence combustion. Therefore, only molecules which have completed gas reaction and combustion reach the surface of the oxide semiconductor. For this reason, the gas reaching the sensor surface will not still be in the noncombusted state. As a result, the sensor can immediately react to changes in the composition of the ambient gas. Furthermore, the sensor itself can be micropatterned in accordance with a thin film micropatterning technique so as to obtain a sensor having dimensions of, for example, 1.5×1.55 ×0.2 mm. As a result, power required for sensor operation is as low as within 5 W. Furthermore, the microheater is built into the oxygen sensor, so that the sensor of this type can be normally operated across the range from a low temperature unlike the conventional oxygen sensor which is not operated at the start of the engine or in idling to a high temperature.

The present invention will be described in detail by way of examples.

EXAMPLE 1

A thin $TiO_2$ film was formed by a bipolar RF sputtering apparatus on an $Al_2O_3$ substrate having dimensions of $30\times30\times0.2$ mm. The $TiO_2$ film consisted of a rutile type $TiO_2$ sintered body of 99.9% or more % purity as a target having a diameter of 110 mm and a thickness of 5 mm. The sputtering conditions were given as follows:

Vacuum pressure: $2\times10^{-6}$ TORR
Vacuum pressure in Ar atmosphere: 3 to $5\times10^{-3}$ TORR
Input power: 200 W
Reflected power: 20 W
Film thickness: 2,000 to 3,000 Å
Sputtering time: 45 minutes.

After the thin $TiO_2$ film was formed on the $Al_2O_3$ substrate, the resultant structure was heated in the air at a temperature of 1,000° C. for about one hour.

Figure 2:
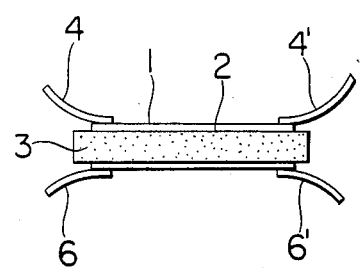
Figure 3:
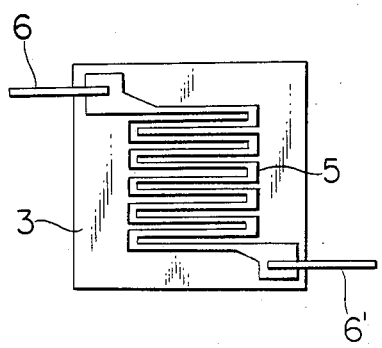

A photoconductive resin was applied to the upper and lower surfaces of the $Al_2O_3$ substrate. By using the photoconductive resin patterns as masks, an interdigital electrode pattern was formed on the surface which had the $TiO_2$ film, and the heater pattern was formed on the opposing surface. Thereafter, Pt was sputtered for about one hour under the same sputtering conditions as described above. In this case, a deposited Pt film had a thickness of about 1 μm. When the photoconductive resin pattern was removed, the Pt electrodes and Pt heater were prepared. Thereafter, the resultant structure was cut by a dicing cutter into dimensions of 1.55×1.50 mm, and Pt wires each having a diameter of 50 μm were bonded to the electrodes, thereby obtaining lead wires. FIGS. 1 to 3 show the sensor manufactured as described above. FIG. 1 is a plan view of the sensor which shows the Pt electrodes; FIG. 2 is a side view of the sensor; and FIG. 3 is a bottom view of the sensor which shows the heater portion. Referring to FIGS. 1 to 3, reference numeral 1 denotes interdigital Pt electrodes of the sensor; 2, a $TiO_2$ film; 3, an $Al_2O_3$ substrate; 4 and 4', Pt lead wires leading from the Pt electrodes 1, respectively; 5, a Pt heater; and 6 and 6', lead wires connected to the Pt heater 5.

The oxygen detection portion and the lead wire portions of the sensor having the structure described above were coated with a porous ceramic coating agent having a catalyst as an additive. Meanwhile, a dense coating agent (e.g., alumina adhesive) was coated on the heater portion so as to prevent the heater portion from receiving any influence from the atmospheric gas.

Figure 4:
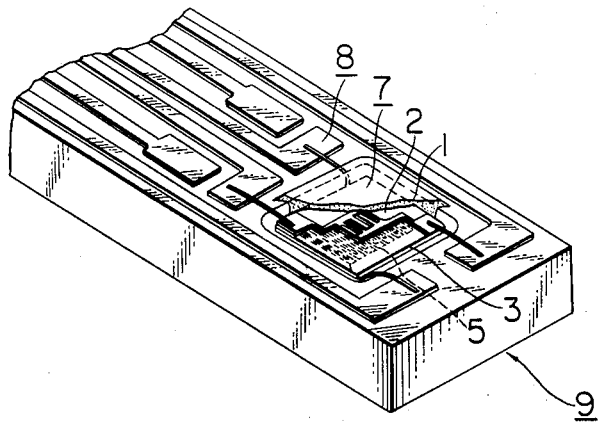
FIG. 4 is a perspective view of an oxygen sensor mounted on an $Al_2O_3$ holder.

The sensor obtained as described above was fixed on an $Al_2O_3$ holder 9 connected to Pt lead wires 8, as shown in FIG. 4. Referring to FIG. 4, reference numeral 7 denotes a porous ceramic layer which contains a catalyst.

Figure 5:
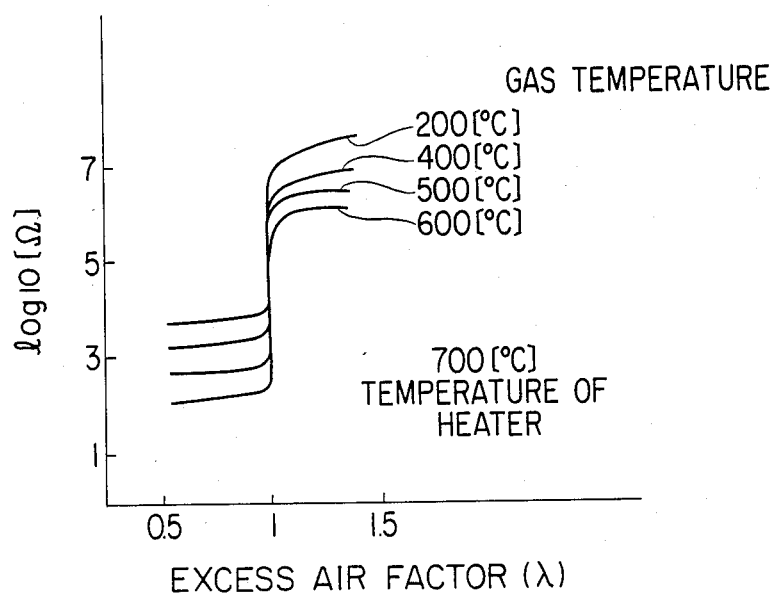
FIG. 5 is a graph showing the characteristics of the oxygen sensor when a heating temperature is used as a parameter.

The characteristics of the sensor as described above were examined. FIG. 5 is a graph for explaining sensor resistance R as a function of excess air factor λ when the temperature of the heater for heating the sensor is used as a parameter. The excess air factor λ is plotted along the axis of abscissa, and the logarithm of the resistance $\log_{10}R$ is plotted along the axis of ordinate.

Figure 6:
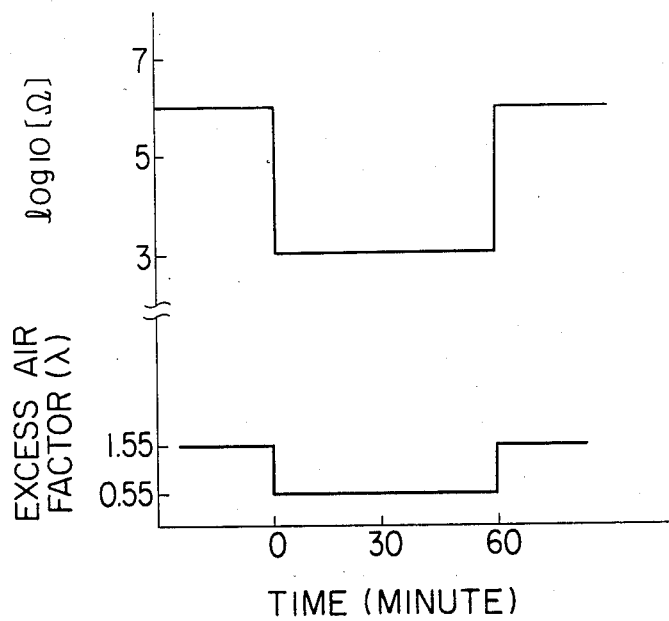
FIG. 6 is a graph showing the change in sensor resistance when the sensor is exposed at the excess air factor λ of 0.55 and at an exhaust gas temperature of 200° C., and the reproducibility of the sensor resistance when the excess air factor λ is changed to 1.55.
Figure 9:
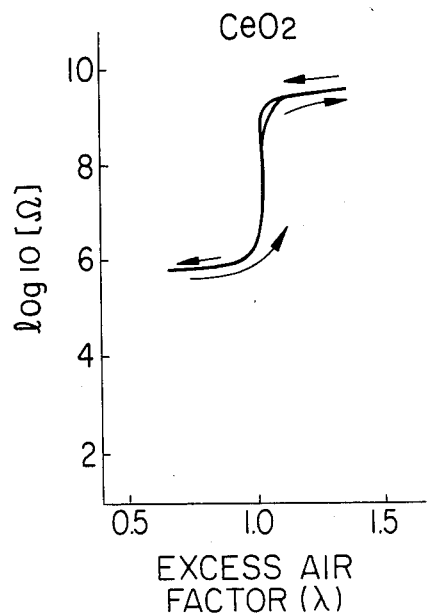
FIGS. 9. to 12 are graphs for explaining changes in resistance as a function of changes in the excess air factor when respective oxide semiconductors comprise $CeO_2$, $SnO_2$, $Nb_2O_5$ and ZnO, respectively.
Figure 10:
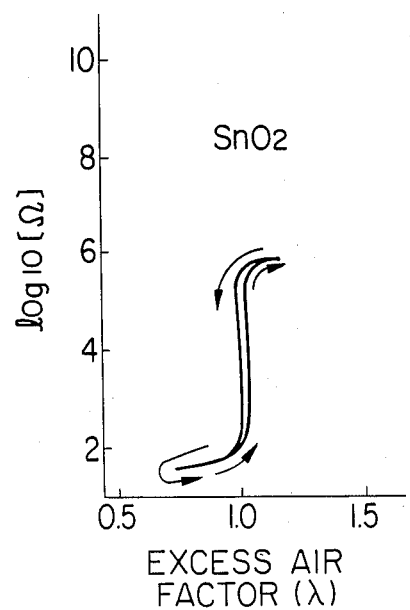
Figure 11:
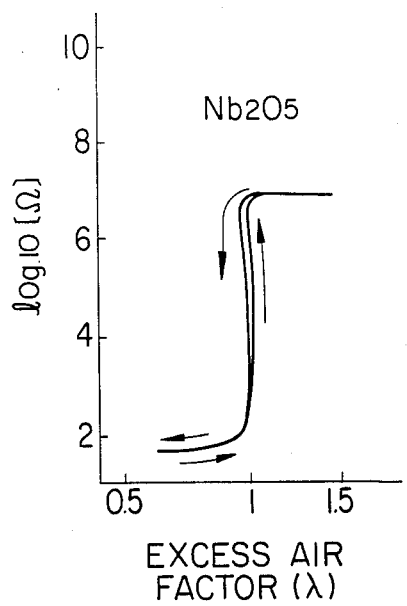
Figure 12:
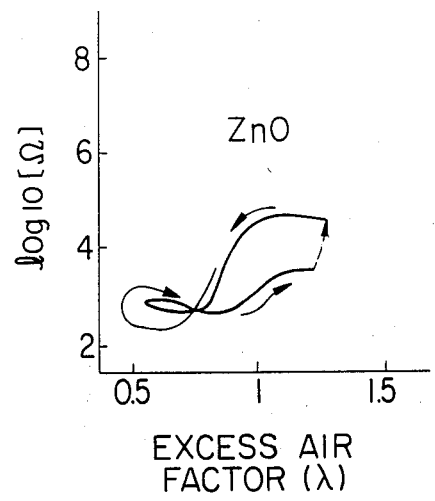

In order to examine the influence of the noncombusted components, sensors having different carried catalysts were exposed in an atmosphere at an excess air factor λ of 0.55 and at an exhaust gas temperature of 200° C. Under these conditions, the changes in sensor resistance was examined. Furthermore, the excess air factor λ was changed to 1.55, and the reproducibility of the changes in sensor resistance was examined. FIG. 6 is a graph for explaining the resistance and the excess air factor as a function of time. Test results are summarized in Table 1 below.

TABLE 1

| Carried catalyst | Content [g/sensor] | Range of change in resistance at a gas temperature of 200 [°C.] (heater temperature: 700° C.) | Stability at λ = 0.55 and reproducibility as λ changes from 0.55 to 1.55 | Evaluation |
|---|---|---|---|---|
| Pt | $5 \times 10^{-5}$ | about 5 digits | Good at a heater temperature of 400° C. Poor at a heater temperature of 500 to 700° C. | Δ |
| Pd | $5 \times 10^{-5}$ | about 5 digits | Good at a heater temperature of 400 to 800° C. | o |
| Rh | $5 \times 10^{-5}$ | about 5 digits | Good at a heater temperature of 400 to 800° C. | o |
| Pt:Rh = 9:1 | $5 \times 10^{-5}$ | about 5 digits | Good at a heater temperature of 400 to 800° C. | o |
| Pt:Rh = 5:5 | $5 \times 10^{-5}$ | about 5 digits | Good at a heater temperature of 400 to 800° C. | o |
| Pt:Rh = 5:5 | $5 \times 10^{-5}$ | about 5 digits | Poor at a heater temperature of 400 to 700° C. | x |
| Pt:Rh = 9:1 | $5 \times 10^{-5}$ | about 5 digits | Good at a heater temperature of 400 to 600° C. and poor at a heater temperature of 700 to 800° C. | Δ |
| None | 0 | about one digit | Great hysteresis and no reproducibility | x |

According to the results shown in Table 1, the degree of variation in the sensor resistance at a gas temperature of 200° C. does not greatly vary according to the types of catalysts carried on the porous layer. However, when the stability of the resistance of the sensor exposed in a very rich (λ=0.55) atmosphere and the reproducibility of changes in the sensor resistance when the rich atmosphere (λ=0.55) was changed to a lean atmosphere (λ=1.55) are examined, the influence of the noncombusted gas components can be completely eliminated when a catalyst such as Pd, Rh, Pt or a mixture of at least two thereof is used.

EXAMPLE 2

The thin $TiO_2$ film was formed on the $Al_2O_3$ substrate in the same manner as in Example 1. A thin film heater was formed on one major surface. On the other hand, a porous ceramic film which carried a catalyst was formed on a sensor portion so as to prevent the sensor portion from being influenced by noncombusted components. The reproducibility and stability of the resistance of the sensor differs in accordance with the type of catalyst. The present inventors found that catalysts such as Pd, Rh, Pt and a mixture of at least two thereof effectively activated the noncombusted components. The present inventors then examined a proper content of the catalyst.

The change in resistance with respect to the change in the air-fuel ratio was examined with the catalyst content used as a parameter (i.e., the air-fuel ratio was changed from a rich ($\lambda=0.95$) ratio to a lean ratio ($\lambda=1.05$). Results are shown in FIG. 7 and 8.

As may be apparent from the graphs shown in FIGS. 7 and 8, it is preferred that a catalyst content falls within the range of 0.001 wt % to 50 wt %. When the catalyst content is smaller than 0.001 wt %, the degree of variation in the resistance is reduced, and the sensitivity is degraded. However, when the catalyst content is greater than 50 wt %, the conductivity of the ceramic film is greatly increased by the catalyst, resulting in an extremely low resistance similar to that obtained in a short circuit. The degree of variation in the resistance is slight.

EXAMPLE 3

Thin $CeO_2$, $Nb_2O_5$, $SnO_2$, and $ZnO$ films were respectively formed on $Al_2O_3$ substrates under the same sputtering conditions as in Example 1 so as to examine possible effective materials other than $TiO_2$ for the oxygen sensor. Each thin film had a thickness of about 2,000 to 5000 Å. Thus, thin film oxygen sensors with various heaters were respectively prepared. Changes in resistance with respect to changes in the excess air factor were examined.

Results are shown in FIGS. 9 to 12. As may be apparent from FIGS. 9 to 12, $CeO_2$, $Nb_2O_5$ and $SnO_2$ besides $TiO_2$ show great changes in resistance without any hysteresis when the excess air factor $\lambda$ is changed in an order of 1.5, 0.5 and 1.5. However, the thin ZnO film sensor has a significant hysteresis and poor reproducibility when the excess air factor changes. It is found that $Nb_2O_5$, $CeO_2$ and $SnO_2$ besides $TiO_2$ are suitable as thin film oxygen sensors.

EXAMPLE 4

As described in Examples 1 to 3, the porous ceramic film (catalyst layer) which carries the catalyst for controlling the gas reaching the surface of the sensor is the main feature of the present invention. The average diameter of the pores in ceramic films according to various coating methods are shown in Table 2 below.

TABLE 2

Relationship Between Coating Method and Average Pore Diameter of Coated Films

| Coating Method | Average pore diameter |
|---|---|
| (1) flame spray coating (spinel powder having a particle diameter of 0.1 to 10 [μm]) | 0.14 μm |
| (2) coating by high-rate sputtering in Ar atmosphere (the substrate is not heated) | 0.01 μm |
| (3) coating by high-rate sputtering in an atmosphere having a gas mixture of Ar (4) and $O_2$ (1) (the substrate is not heated) | 0.001 μm |
| (4) dipping (powder having a particle diameter of 0.1 to 7 [μm]) | 1 to 2 μm |

Figure 13:
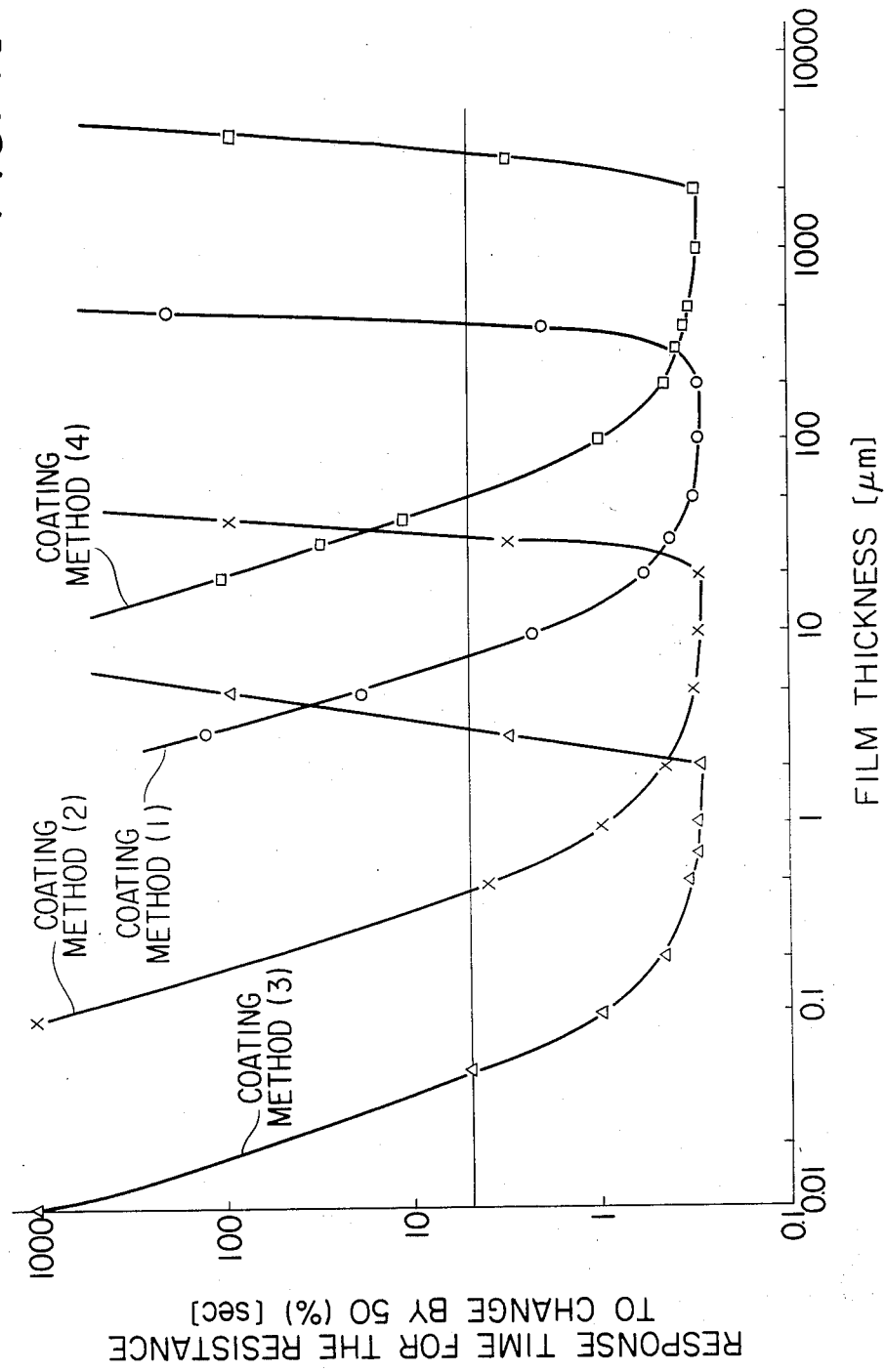
FIG. 13 is a graph for explaining the thickness of the catalyst coating as a function of the response time.

Sensors were prepared having porous ceramic films (each carrying 5 wt % of Pd) of varying film thickness in accordance with the coating methods described above. These sensors were exposed in a lean atmosphere ($\lambda=1.5$) at a temperature of 600° C. for 5 minutes. The sensors were then placed in a rich ($\lambda=0.5$) exhaust gas atmosphere for one hour so as to examine the relationship between the response time and the film thickness. The results are shown in FIG. 13. The relationship between the film thickness and the response time is summarized in Table 3 when the various coating methods are respectively used as parameters.

TABLE 3

| Ratio of Film thickness t to Pore diameter r | 20 | 50 | 200 | 700 | 2000 | 3000 | 4200 |
|---|---|---|---|---|---|---|---|
| Time for the resistance to change by 50 [%] | 120 sec | 5 sec | 450 msec | 300 msec | 300 msec | 5 sec | 140 sec |
| Evaluation | x | Δ | o | o | o | Δ | x |

The ratio t/r of the film thickness t to the pore diameter r preferably falls within the range of 50 to 3,000. The time required for the sensor resistance to change by 50% falls within the range of 50 msec to 5 sec.

What is claimed is:

1. A thin film oxygen sensor for furnishing an output signal indicating whether the excess air factor is larger or smaller than 1, said sensor comprising:
   a substrate having opposite surfaces;
   a sensor portion on one of said surfaces of said substrate and including an oxide semiconductor;
   a microheater on the opposite said surface of said substrate; and
   a porous catalyst layer on said sensor portion and having a thickness and an average pore diameter such that the ratio of said thickness to said average pore diameter falls within the range of 50 to 3000, whereby non-combusted components are combusted within said porous catalyst layer thereby furnishing said output signal stably and accurately.

2. A sensor according to claim 1 wherein said catalyst layer contains a catalyst component selected from the group consisting of palladium, rhodium, platinum and a mixture of at least two thereof, and the amount of said catalyst component in said layer is within a range of 0.001 wt % to 50 wt %.

3. A sensor according to claim 1, wherein said oxide semiconductor comprises a material selected from the group consisting of titanium dioxide ($TiO_2$), niobium pentoxide (Nb$_2$O$_5$), cerium dioxide (CeO$_2$) and stannic oxide (SnO$_2$).

4. A sensor as claimed in claim 1 further comprising means for applying a voltage to the oxide semiconductor, and means for measuring an output voltage across said semiconductor as an output signal according to the changing resistance of said semiconductor based on the oxygen content of a sampled, combusted gas from the exhaust of an engine.

5. A sensor as claimed in claim 4 wherein the thickness of the catalyst layer is such to effect substantially complete combustion of any non-reacted oxygen whereby the gas reaching the surface of the oxide semiconductor will not be in non-combusted state.

* * * * *